(12) United States Patent
Hirsh

(10) Patent No.: US 10,918,300 B2
(45) Date of Patent: Feb. 16, 2021

(54) NON-INVASIVE SYSTEM AND METHOD FOR MONITORING LUSITROPIC MYOCARDIAL FUNCTION IN RELATION TO INOTROPIC MYOCARDIAL FUNCTION

(71) Applicant: COOPER HEALTH SYSTEM, Camden, NJ (US)

(72) Inventor: Robert Alan Hirsh, Merion Station, PA (US)

(*) Notice: Subject to any disclaimer, the term of this patent is extended or adjusted under 35 U.S.C. 154(b) by 213 days.

(21) Appl. No.: 16/108,846

(22) Filed: Aug. 22, 2018

(65) Prior Publication Data

US 2018/0360338 A1    Dec. 20, 2018

Related U.S. Application Data

(62) Division of application No. 15/288,455, filed on Oct. 7, 2016, now Pat. No. 10,085,665.

(Continued)

(51) Int. Cl.
| | |
|---|---|
| *A61B 5/0452* | (2006.01) |
| *A61B 5/044* | (2006.01) |
| *A61B 7/04* | (2006.01) |
| *A61B 5/11* | (2006.01) |
| *A61B 5/00* | (2006.01) |
| *A61B 5/04* | (2006.01) |

(52) U.S. Cl.
CPC ............ *A61B 5/0452* (2013.01); *A61B 5/002* (2013.01); *A61B 5/0022* (2013.01); *A61B 5/044* (2013.01); *A61B 5/04017* (2013.01); *A61B 5/1107* (2013.01); *A61B 7/04* (2013.01); *A61B 5/7257* (2013.01); *A61B 2562/0219* (2013.01)

(58) Field of Classification Search
CPC ....... A61B 5/0452; A61B 7/04; A61B 5/1107; A61B 5/0022; A61B 5/002; A61B 5/04017; A61B 5/044; A61B 2562/0219; A61B 5/0757; G16H 40/67
See application file for complete search history.

(56) References Cited

U.S. PATENT DOCUMENTS

| 7,054,679 B2 | 5/2006 | Hirsh |
| 7,267,649 B2 | 9/2007 | Zdeblick |
| (Continued) | | |

OTHER PUBLICATIONS

Title: American Society of Anesthesiologists Abstract Published By: Robert A. Hirsh, M.D., Marc C. Torjiman, Ph.D., Roy D. Goldfarb, PH.D. Dated: Oct. 15, 2011.

(Continued)

*Primary Examiner* — Catherine M Voorhees

(57) ABSTRACT

A system and method for non-invasively monitoring the hemodynamic state of a patient by determining on a beat-by-beat basis the ratio of lusitropic function to inotropic function as an index of myocardial well-being or pathology for use by clinicians in the hospital or by the patient at home. In one embodiment of the system a smartphone running an application program that is connected through the internet to the cloud processes electronic signals, first, from an electrocardiogram device monitoring electrical cardiac activity, and second, from a seismocardiogram device monitoring mechanical cardiac activity in order to determine such ratio as an instantaneous measurement of the hemodynamic state of the patient, including such states as sepsis, myocardial ischemia, and heart failure.

14 Claims, 2 Drawing Sheets

Related U.S. Application Data

(60) Provisional application No. 62/238,330, filed on Oct. 7, 2015.

(56) References Cited

U.S. PATENT DOCUMENTS

| | | | |
|---|---|---|---|
| 7,657,306 B2 | 2/2010 | Hirsh | |
| 7,689,283 B1 * | 3/2010 | Schecter | A61B 7/00 607/18 |
| 7,761,141 B2 | 7/2010 | Hirsh | |
| 8,843,194 B2 | 9/2014 | Hirsh | |
| 2007/0191724 A1 * | 8/2007 | Hirsh | A61B 5/029 600/523 |
| 2009/0124867 A1 * | 5/2009 | Hirsh | A61M 16/0051 600/301 |
| 2010/0168578 A1 * | 7/2010 | Garson, Jr. | A61B 8/0858 600/443 |
| 2015/0359489 A1 | 12/2015 | Baudenbacher et al. | |

OTHER PUBLICATIONS

Title: Biostamp Temporary Tattoo Electronic Circuits by MC10 Published in: Dezeen Magazine URL: http://www_dezeen.com/2013/03/28/biostamp-temporary-tattoo-wearable-electronic-circuits-john-rogers-mc10/ Dated: Mar. 28, 2013.

Title: Heart Activity Monitoring on Smartphone Published By: Anh Dinh Published in: 2011 International Conference on Biomedical Engineering and Technology PCBEE vol. 11 (2011) © (2011) IACSIT Press, Singapore.

Title: Detection of S1 and S2 Heart Sounds by High Frequency Signatures Published by: D. Kumar, P. Carvalho, M. Antunes, J. Henriques, L. Eugenio, R. Schmidt, J. Habetha Published in: Proceedings of 28th IEEE EMSS Annual International Conference Published City: New York, USA Dated: Aug. 30-Sep. 3, 2006, pp. 1410-1416.

Title: Influence of Altered Inotrophy and Lusitrophy on Ventricular Pressure-Volume Loops Published by: Arnold M. Katz, MD, FACC Published in: Basic Concepts in Cardiology; JACC vol. 11, No. 2 Dated: Feb. 1988.

Title: [The long QT syndrome: importance of phonocardiography and ergometry] Published by: E Dupasouier and A. Nicole, L. Pinget Published in: U.S. National Library of Medicine National Institutes of Health URL: http://www.ncbi.nlm.nih.gov/pubmed/2880395 Dated: Jan. 3, 1987.

Title: Structural Relationships Between Measures Based on HeartI3eat Intervals: Potential-tor Improvedlirsk Assessment Published by: Alfred P. Hallstrom, Phyllis K. Stein, Raphael Schneider, Morrison Hodges, Georg Schmidt, and Kurt Ulm Published in: IEEE Transactions on Biomedical Engineering, vol. 51, No. 8 Aug. 2004, pp. 1414-1420.

Title: Development of a secure body area network for a wearable physiological monitoring system using a PSoC Drocessor Published by: N. Sriraam, S. Swathy and S. Vvijayalakshmi Published in: Journal of Medical Engineering & Technology, 2012; 36: 28-33.

Title: Relationships Between the Electrocardiogram and Phonocardiogram: Potential for Improved Heart Monitoring Published by: L.S. Stodieck and M. W. Luttges Published in: ISA Transactions, vol. 23, No. 4 1984.

Title: Le syndrome QT long: importance de la phonocardiographie et de l'ergomelric Published by: E. Dupasquier and A. Nicole, L. Pinget Published in: Schweizerische Medizinische Wochenschrift Journal; 117: 17-22 Dated: 1987 published location: France.

Title: A Survey on Wearable Sensor-Based Systems for Health Monitoring and Prognosis Jublished by: Alexandros Pantelopoulos and Nikalaos G. Bourbakis Dublished in: IEEE Transactions on Systems, Man, and Cybernetics—Part C: Applications and Reviews, vol. 40, No. 1, Jan. 2010.

* cited by examiner

NON-INVASIVE SYSTEM AND METHOD FOR MONITORING LUSITROPIC MYOCARDIAL FUNCTION IN RELATION TO INOTROPIC MYOCARDIAL FUNCTION

CROSS REFERENCE TO RELATED APPLICATION

The present application is a division of pending U.S. patent application Ser. No. 15/288,455, filed Oct. 7, 2016, and entitled Non-Invasive System and Method for Monitoring Lusitropic Myocardial Function in Relation to Inotropic Myocardial Function, which is incorporated by reference in its entirety herein. As such, this application claims the benefit of U.S. Provisional Application No. 62/238,330 filed Oct. 7, 2015.

FIELD OF THE INVENTION

The instant invention relates to a non-invasive system and method to monitor cardiac parameters, specifically lusitropic myocardial function in relation to inotropic myocardial function on a beat by beat basis in order to assess myocardial well-being or pathology on a real time basis.

BACKGROUND OF THE INVENTION

1. The Problem to be Solved

Lusitropic function is the ability of the left ventricle to relax during diastolic filling, following maximal left ventricular tension, and ejection of the stroke volume with each heartbeat during systole. Inotropic function is the ability of the myocardium to develop tension and pressure in the left ventricle during systole. Quantifying lusitropic function, and lusitropic function in relation to inotropic function, is the key to quantifying acute conditions, such as myocardial ischemia, myocardial infarction, and sepsis. At present, there is no non-invasive way to quantify lusitropic function during the relaxation and filling phase of the cardiac cycle. Nor is there such a way to quantify lusitropic function in relation to inotropic function on a beat-by-beat basis.

At present, the state-of-the-art in the measurement of myocardial ischemia consists in the measurement of ST segment elevations or depressions on an EKG. Modern technology has permitted the use of computer learning devices that can measure the baseline ST segment position, and report to the operator any upward or downward deviation in the ST segment (in mm) that may evolve during surgery, or during an ICU stay. This technology misses a large fraction of the episodes of ischemia that may occur in parts of the heart whose electrical vectors are not well aligned with the electrical axes represented by the EKG leads that are being monitored, typically Lead II and Lead V.

Also, modern trials of new medications for the treatment of sepsis have suffered from the lack of a clear clinical decision point early in the natural history of sepsis that defines precisely when to use a drug, and on precisely whom to use it.

Inotropic function can be measured invasively as the maximal value of the first derivative of left ventricle ("LV") pressure during systolic contraction. Conversely, lusitropic function can be quantified as the absolute value of the most negative dip in the first derivative of LV pressure during diastolic relaxation. In the ASA Abstract published by the inventor, Torjman, and Goldfarb, in 2011 (the "Abstract"), a pig model of sepsis showed a clear and sudden reversal in the ratio of lusitropy to inotropy on a beat-to-beat basis, from greater than 1 to less than 1 exactly 14 minutes after the experimental placement of a clot of specially chosen E. Coli bacteria in the peritoneum of the pig. This is likely due to the signal effects of the interleukin storm that precedes frank sepsis, upon the contractile nano-machinery of the myocardium. The brevity of that 14-minute interval is constitutes an important step forward in monitoring heart problems. By contrast, conventional metrics of cardiodynamic function such as blood pressure, stroke volume, or cardiac output take hours before they show signs of deterioration during experimental sepsis. So, the data shows that this ratio of lusitropic to inotropic function can serve as an early warning sign of cardiac decompensation in sepsis. But in the experiment, this required the invasive placement of a solid-state pressure transducer at the end of a catheter directly into the left ventricle. If it were possible to detect this inversion of the ratio of lusitropy to inotropy cheaply, routinely, and non-invasively, then clinicians would be empowered to treat each patient with sepsis with appropriate medication, however expensive it may be, with high reliability, sensitivity, and with few false positives and false negatives. In other words, the "number needed to treat" ("NNT"), would be low. This new capability would remove a great deal of the "noise" in clinical trials of new medications for the treatment or palliation of sepsis. That, in turn, would allow any clinical trials of new medications to be conducted conclusively, on small numbers of patients, in significantly less time, and at much lower cost than is possible at present. This should be of great interest to the pharmaceutical industry.

Moreover, at the present time, there is no inexpensive, convenient, continuous way to monitor, or precisely quantify the natural history of congestive heart failure, understood as inotropic failure, or heart failure without preservation of ejection fraction. Similarly, there is no such way to monitor or quantify the natural history of diastolic heart failure, understood as lusitropic heart failure, or heart failure with preservation of ejection fraction ("HFpEF"). The latter category accounts for about 50% of all cases of heart failure. Such a capability would be useful as new and better drugs and treatments emerge over time. This advancement would also be useful for hospice and palliative care, as a way of sharpening prognosis in these usually fatal conditions and would be of interest to the life insurance industry as a low cost method of risk assessment.

2. A Description of the Prior Art

In addition to the Abstract, the inventions relating to non-invasive methods of monitoring cardiac parameters that are disclosed in the following patents to Hirsh, the inventor of the instant invention, relate to the field of the instant invention: U.S. Pat. Nos. 7,761,141, 7,054,679, 7,657,306, and 8,843,194 (the "'194 Patent"). Certain hardware technology relevant to the system of the present invention is described in the New York Times Article of Oct. 9, 2014 by Nick Bilton titled "Wearable Technology, Warts and All," as well as in the Anh Dinh article from the 2011 Conference on Biomedical Engineering and Technology titled "Heart Activity Monitoring on Smartphone."

SUMMARY OF THE INVENTION

Researchers have worked to develop non-invasive methods to measure cardiac output and indices of preload and afterload; however, to date there is no solution that allows for non-invasive measurement of lusitropy, except as it relates to acute myocardial ischemia, where lusitropy rapidly and dramatically decreases, and only then, as shown by the depression or elevation of the ST segment of an EKG with ischemia. Nor has anyone solved the problem of determining in a non-invasive way the beat-by-beat relationship between inotropy and lusitropy as an index of myocardial well-being or pathology.

The overriding issue is that by the time these other metrics, such as blood pressure, cardiac output, or stroke volume, start to diminish acutely, the patient is already well along his way down the slippery slope of decompensation and death.

The instant invention based on non-invasive monitoring provides for real time diagnosis and treatment of the following cardiac problems:

A. The sepsis studies show that in sepsis, lusitropy, in relation to inotropy, declines in a sentinel fashion, well before these other metrics. This new invention gives clinicians more time to intervene.

B. Similarly, in the context of myocardial ischemia, an ST-segment depression is a late sign of an imbalance between oxygen supply and demand, in favor of demand. It is well known that regional wall motion abnormalities ("RWMAs") on a two dimensional echocardiographic image of the left ventricle in cross section precede ST-segment depression by several minutes. It is likely that a decline in lusitropic function precedes RWMAs in the context of myocardial ischemia. That would give clinicians a longer window of opportunity in which to restore oxygen supply and demand balance, and allow them to prevent myocardial ischemia and infarction in the first place.

C. Noninvasive measurement of the relation between lusitropy and inotropy can serve to diagnose and monitor heart failure and HFpEF, also known as diastolic heart failure. At present, diastolic heart failure is diagnosed when a patient has signs and symptoms of heart failure, but has a normal ejection fraction on two dimensional echocardiogram. Alternatively, an elevated BNP level in the presence of a normal ejection fraction or stress echocardiogram is necessary to make the diagnosis. The present invention represents a cheaper, more reliable way to make the diagnosis and quantify the natural history and treatment of HFpEF. It uses real time physiologic metrics rather than imaging or laboratory values of blood biomarker concentrations. In the prior art there are no teachings on how to make myocardial lusitropy the subject of routine noninvasive clinical assessment, particularly in a way that is dynamical, and not anatomical or volumetric. The present invention is founded upon a novel and recently predicted and demonstrated principle of physiology. Up until now, the LV was a clinical 'black box' with respect to actual pressure measurements, and time derivatives of pressure measurements, except for short periods of time in the cardiac catheterization laboratory. The procedure done there is hazardous, with risk for fatal arrhythmias, infection, and hemorrhage. It uses expensive disposables, and generates a great deal of infectious waste, whose disposal is expensive. Cardiac catheterization is only undertaken by highly trained—and highly compensated—interventional cardiologists. It is certainly not at all well suited to clinical monitoring, let alone telemedicine. The present technology, by contrast, is very well suited to the enterprise of telemedicine.

In the '194 Patent, the inventor of the present invention taught that, based on the experimentation results set forth therein, there exists an electromechanical interval (E–M) where the E-event is defined by the time of the second derivative maximum represented near the Q-wave in the QRS complex of the EKG. The M-event is defined as the time of the second derivative maximum of the peripheral pulse pressure wave, as detected by a radial or other peripheral arterial catheter pressure transducer. The patent teaches, among other things, that 1/(E–M) is linearly proportional to the natural logarithm of the maximum value of the first derivative of systolic pressure in the left ventricle. That is, $$\ln(LVP'\text{ max}) = A + B/(E-M),$$

where A, B are personal constants.

While this methodology works well in patients who are having surgery under anesthesia, or patients in ICU beds, it is not well suited to measurements on ambulatory patients because the wrist can be arrayed with many degrees of freedom at many levels with respect to the heart. The resulting changes in DC hydrostatic pressure in the column of vertical fluid between the heart and the transducer has a huge effect on the speed of the pulse wave, and hence on the time differential, (E–M). The torsional, flexional, and extensional motions of the wrist play havoc with acoustic or mechanical coupling between the skin-mounted transducer and the pressure wave in the underlying artery.

Moreover, it is extremely difficult to transduce the radial arterial pulse wave through skin over the radial artery using existing transducer technology. The signal to noise ratio of extant accelerometers or strain gauges is too low to make a clinically reliable measurement. Finger cuffs (Edwards' 'Nexfin') and electro-mechanically applanated piezoelectric transducers (Tensys Medical's 'T-Line') have been used, with some end-user and reliability obstacles, to measure blood pressure and other hemodynamic parameters. So in order to measure the inotropic function of the heart on an ambulatory basis, it is necessary to find another, non-invasive, way to determine the M-event, which is described herein.

By allowing lusitropic function to be quantified non-invasively, the present invention can serve to inexpensively, safely, and reliably diagnose and monitor HFpEF, as well as the efficacy, or inefficacy of therapeutic medications and procedural interventions for cardiac problems across the spectrum. It is also key to quantifying chronic conditions characterized by poor lusitropic function, such as diastolic heart failure, or HFpEF, and its several causes, such as hypertension, diabetes, aortic stenosis, constrictive pericarditis, and restrictive cardiomyopathy, including amyloidosis, sarcoidosis and fibrosis. By allowing lusitropic function to be quantified non-invasively, the present invention can serve to inexpensively, safely, and reliably diagnose and monitor HFpEF, as well as the efficacy, or inefficacy of therapeutic medications and procedural interventions. The technology can serve in one embodiment as a bedside monitor in hospital, or, combined with smartphone and internet connectivity, the invention can also serve in another embodiment as a new window into myocardial function in the emerging world of telemedicine, helping to deliver better, faster, cheaper, safer care, in a way that radically increases access to care for large communities of people who are not now being well served by the existing health care system. This telemedical measurement, characterization, and cloud storage of the patient's 'Physiome' data, owned by the patient, is well described in Dr. Eric Topol's recent book, 'The Patient Will See You Now' (Basic Books, 2015).

DETAILED DESCRIPTION OF THE INVENTION

Figure 1:
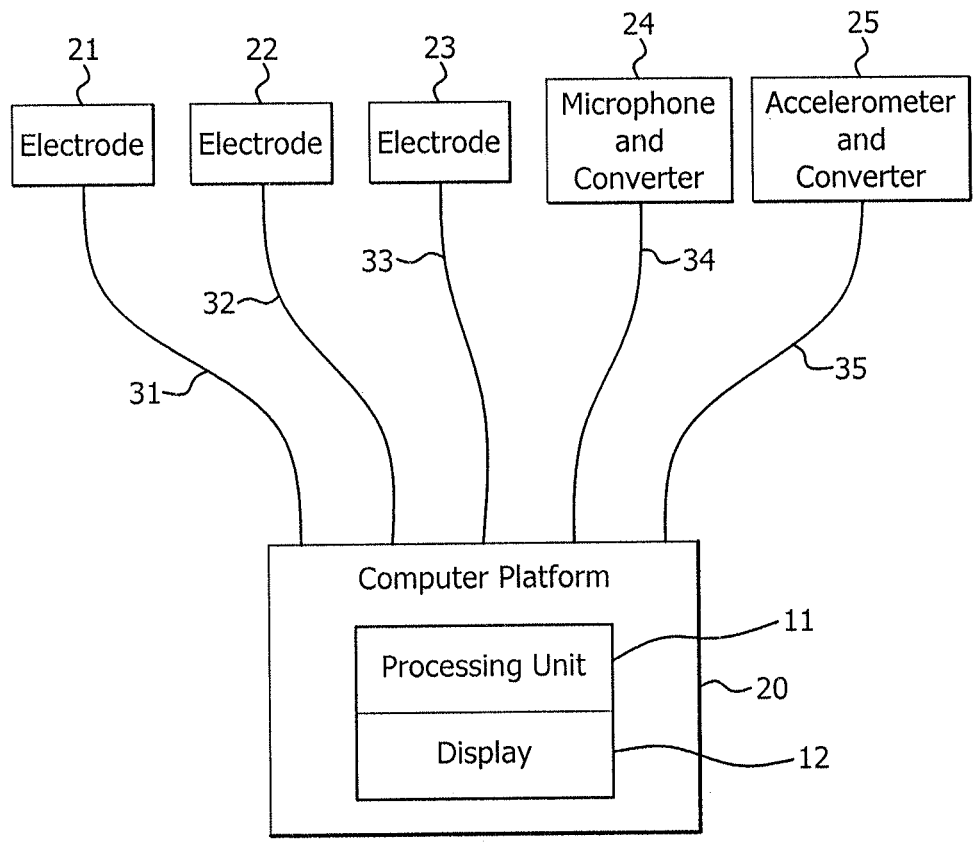
FIG. 1 is a block diagram of one embodiment of the non-invasive system of the present invention.

One object of this invention is to provide an inexpensive, safe, continuous, non-invasive, metric based on lusitropic function, and lusitropic function relative to inotropic function on a beat-to-beat basis, that is determined in a non-invasive manner, that allows for continuous monitoring in the emerging smartphone-connected telemedicine space. Another objective is to improve access to care by removing traditional obstacles to clinical assessment and diagnosis by measuring a physiologic cardiodynamic quantity that is not now being measured on a non-invasive basis, whose decompensation results in at least three categories of disease: myocardial ischemia, sepsis, and heart failure, whose costs are huge and whose consequences are devastating. The system of the present invention is comprised of at least one electrocardiographic lead containing an electrode, preferably lead II, but it should be noted that the preferred embodiment employs greater accuracy by using three leads having electrodes 21, 22, and 23 as shown in FIG. 1, those being lead V, and lead I in addition to lead II, by which electronic signals measuring electrical activity of the heart are obtained and digitized; a phonocardiogramic signal, obtained from a microphone 24 placed directly over the heart on the chest, and/or a seismocardiogramic signal, obtained from an accelerometer 25 placed directly over the heart, each of which having therein a converter as identified in boxes 24 and 25 in FIG. 1 to convert the mechanical data from the microphone or accelerometer into electronic data which is digitized; and a computer platform 20 in FIG. 1, including a display 12, to run the software needed to process the (i) the digitized electronic data stream that is input from connections to the processor 11 of the computer platform 20 from the electrocardiogram at the same time as (ii) the digitized electronic data stream that has been converted from the mechanical data from the microphone or accelerometer, each of which being input by connections to the processor of the computer platform from the electrical and mechanical systems described above in accordance with the algorithm described in this specification. The computer platform in one embodiment is comprised of a smartphone with internet and cloud connectivity on which the algorithm described herein runs as an application program. The phonocardiogramic devices or seismogramic devices can be used interchangeably, or to complement one another so as to make the measurement more robust. Optionally, this can be in the form of wearable 'skin tattoo' circuitry such as the devices made by MC10, which contain Blue-Tooth connectivity for a microelectromechanical system ("MEMS") microphone as well as MEMS accelerometer transducers as described in the article referenced above. Seismocardiogram technology as described by Anh Dinh, supra, can be conveniently placed on the chest, over the heart, near the point of maximal impact, typically in the $5^{th}$ intercostal space in the mid-clavicular line. FIG. 1 shows the system 10 comprised of three EKG leads 21, 22, and 23 (respectively, lead II, lead V, and lead I) connected to a processing unit 20 through connectors 31, 32, and 33, respectively, to which are also connected a microphone with built in converter 24 through connector 34 and an accelerometer with built in converter 25 through connector 35. In another embodiment, the physical connectors 34 and 35 are replaced by the use of wireless technology, such as Blue Tooth technology, linking the microphone 24 electronic output and/or accelerometer 25 electronic output through directly to the processor 11 in the computer platform 20 of FIG. 1.

The system described above provides non-invasive metrics of inotropic and lusitropic function. Optionally, this system can provide stroke volume and cardiac output information, non-invasively on patients who are bedbound, or ambulatory, via their smartphone connectivity, which information can then be uploaded the to the cloud for processing.

This system can algorithmically extract useful, actionable clinical knowledge about the patient's condition and response to treatment, from a massive amount of data obtained from transducer streams as described and can be used for diagnosis as well as management, that is, to reliably detect useful signal and separate that from noise as described herein.

The goal is to algorithmically detect significant changes in the patient's cardiac status earlier in the natural history of decompensation than is achievable in the prior art, especially in patients known from their prior co-morbidities to be at risk, and to create longer windows of opportunity to intervene, as well as to prevent unnecessary hospitalization with its attendant inconvenience and expense.

The use of the system in the method of the present invention is founded upon a novel and recently predicted and demonstrated principle of physiology as described in the Abstract. The principle will be readily apprehended by review of the Wiggers Diagram, well known to those practiced in the art, which shows the simultaneous traces of EKG, left ventricular pressure ("LVP"), arterial blood pressure ("ABP"), with a phonocardiogram, throughout the cardiac cycle. The lusitropic event, where the myocardium maximally relaxes after systole, is always heralded electrically on the EKG by the T-wave, referred to as the "Lightning." The closure of the aortic valve is audible as S2 in the phonocardiogram which announces to the informed listener that the moment of most rapid loosening of the myocardium in diastole has just occurred, which is referred to as the "Thunder." By measuring the interval, in milliseconds, between the Lightning and the Thunder, it is possible to accurately quantify the lusitropic state of the myocardium because the Lightning-'Thunder', or (E–M) lusi, interval, other things being equal, becomes longer when the heart loses its lusitropic function, providing an accurate metric of the stiffness of the heart muscle in diastole, as the heart relaxes from its full-on contraction state and the LV begins to fill. This ability of the myocardium to relax is lost for instance, during ischemia, simply because relaxation of myocardium after systolic contraction is an oxygen-requiring process, where cross-links between actin and myosin fibrils are broken in an ATP-requiring, energy-requiring process. An ischemic, oxygen-starved heart is a stiff, inelastic heart. Having lost its systolic tension, the ischemic myocardium is unable to spring back to an unfilled state of low wall tension with its usual speed. This change can be accurately measured. Conversely, other things being equal, a heart that is well perfused with high oxygen-content arterial blood, will relax very quickly, and the Lightning-Thunder interval will be measurably shorter.

Similarly, during sepsis, a myocardium that is at the center of an interleukin and acute phase reactant storm, may have one or more of the complex molecular contractile nanomachines that make up the myocardium acutely inhibited in a way that is now measurable, cheap, and harmlessly non-invasive.

And lastly, this present invention brings more precision to the diagnosis of diastolic heart failure, or heart failure with preserved ejection fraction. The value of (E–M) lusi at rest, and with moderate exercise, above a population normalized threshold value, may of itself be diagnostic of HFpEF.

Figure 2:
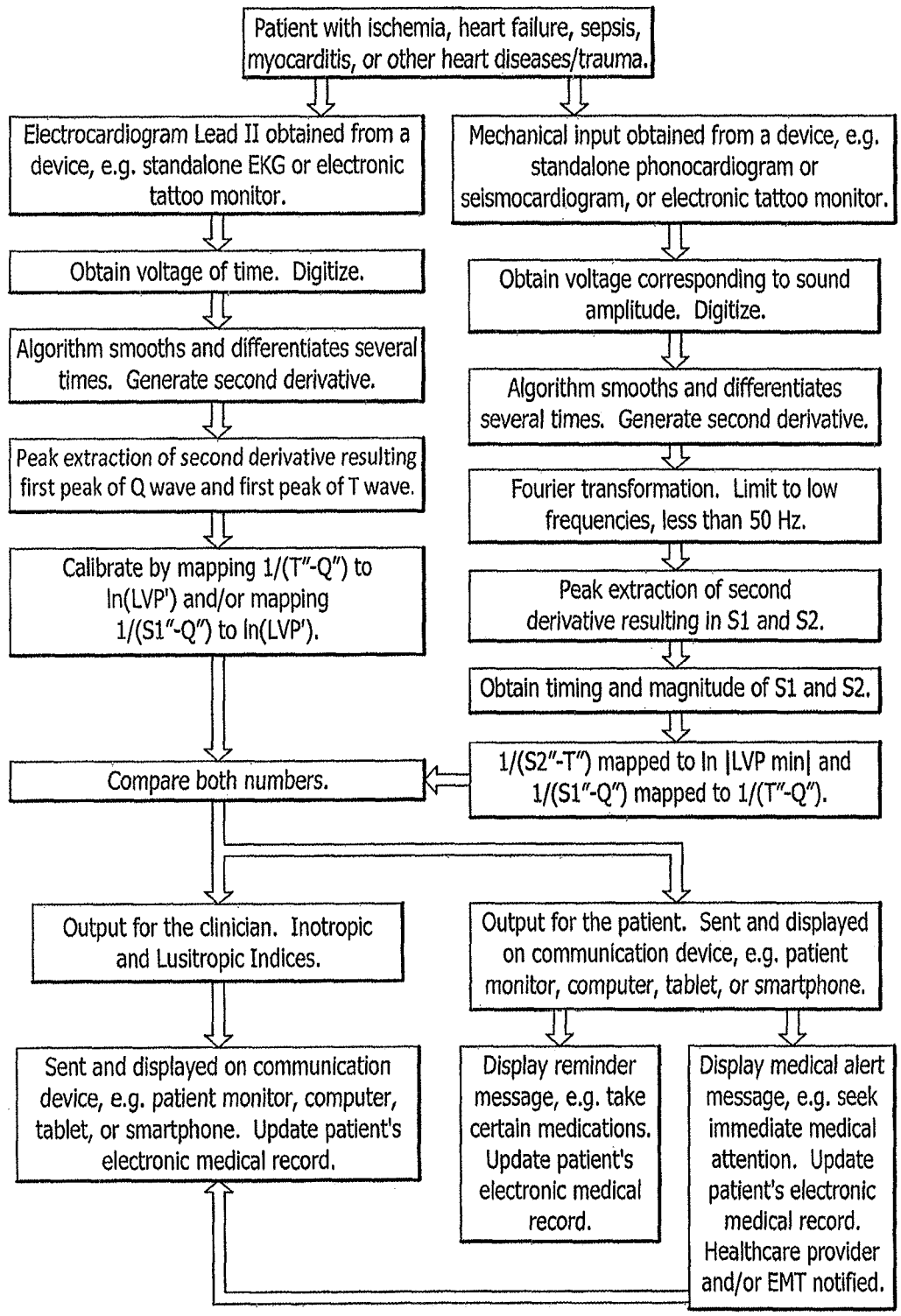
FIG. 2 is a flow chart for non-invasive monitoring of a patient using the algorithm and teachings of the present invention.

FIG. 2 is a flow chart that presents the steps under the control of the algorithm of the present invention used by the presently invented, non-invasive system. A patient with signs of one of a number of possible heart problems or trauma as described therein (such as, without limitation, ischemia, heart failure, sepsis, and myocardis) is non-invasively monitored by the system described above. The left side of the block diagram describes the steps used in the non-invasive collection of electrocardiogram data and generating a number which is related to lusitropic function which are: obtaining voltage measurements as a function of time; digitizing such data; using the algorithm described herein on such data to smooth and provide time derivatives thereof, including the second derivative thereof; extracting the first peak of the Q wave and first peak of the T wave; and calibrating by mapping 1/(T"–Q") to ln(LVP') and/or mapping 1/(S1"–Q") to ln(LVP) which gives the number related to lusitropic function. The right side of the block diagram describes the steps used in the non-invasive collection of mechanical input data and generating a value that is related to inotropic function which are: obtaining a voltage measurements as a function of time corresponding to sound amplitude from the mechanical input device; digitizing such data; using the algorithm described on such data to smooth and provided time derivatives thereof, including, the second derivative thereof; applying the well known methods of Fourier transformation to such function and applying a low pass filter to limit the result to frequencies below 50 hertz; extracting the peak of that function to derive S1 and S2; obtaining the timing and magnitude of S1 and S2; and calibrating by mapping 1/(S2"–T") to ln(abs (LVPmin)) and mapping 1/(S1"–Q") to 1/(T"–Q") which gives the value related to inotropic function. The ratio of the first such value to the second such value provides a measurement of lusitropic myocardial function to inotropic myrocardial function which can then be used by the end user who is either a clinician in a hospital setting, or the patient by himself or herself, while at home.

It should be noted that with respect to the steps of the collection of mechanical input data that the application of the Fourier transform to the voltage as a function of time representing sound can also be effective when such application precedes the smoothing and time derivative operations.

The algorithm referenced above as used by the present system and method can be further explained as follows:
1) In the (E–M)lusi interval, a metric of diastolic function, the E-event is the time of the maximum value of the second derivative of the EKG at first peak of the T-wave.
2) In the (E–M)lusi interval, the lusitropic M-event is the time of the maximum value of the second derivative of the amplitude signal of the phonocardiogram, either pre-cordial, for ambulatory patients, or esophageal in anesthetized or intubated critical care patients. ln(E–M)lusi, the Lusitropic M-event corresponds to the S2 heart sound on the phonocardiogram. This can be seen in the well known Wiggers Diagram.
3) In the (E–M) lusi interval, the lusitropic M-event can also be the maximum value of the first peak in the cardiac seismogram following the second peak in the second derivative of the T-wave on EKG, such as that which is labeled "AC" ("aortic valve closing").
4) Alternatively, the M-event can be the peak in the first or second derivative of the cardiac seismogram following the first peak in the second derivative of the T-wave on EKG.
5) The two embodiments of (E–M) lusi can be measured simultaneously and mapped one against the other, cumulatively in real time. The slope and intercept of this linear relation can be characterized in an epochal or running fashion. This serves to increase the robustness of the system, should there be an interruption in either the phonocardiogram or the cardiac seismogram. The missing data can be interpolated from the ongoing 'calibration' relation between the two species of (E–M) lusi. Each measurement serves as a reality check on the other in a way that is opaque to the end user.
6) To a useful approximation, $$\ln(abs(LVP' \ min)) = A1 + B1/(E-M)lusi \quad \text{Equation 1}$$

In other words, this absolute value of the most negative value of the first derivative of pressure in the left ventricle during diastolic relaxation, is linearly proportional to 1/(E–M)lusi. This will work whether the M-event is derived from phonocardiographic or cardiac seismographic data. Optionally, A1 and B1 can be shown, to a useful approximation, to be empirical functions of height, weight, age, and gender. It may be noted that this is possible, but not necessary, inasmuch as clinicians do not ordinarily trouble themselves to know the values of the first derivative of LVP (LVP' max) in systole, and they will be well served by a numerical index that is monotonically or linearly increasing with respect to LVP' min during diastolic relaxation of the myocardium.
7) The power law that relates the maximum value of the first peak in the second derivative of the T-wave voltage to the absolute value of the maximally negative value of the first derivative of LV pressure in diastole, LVP' min, gives a useful approximation, so that $$\ln(EKG" \ max)_{T-wave} = A2 + B2(\ln(ABS(LVP' \ min))) \quad \text{Equation 2}$$

Since two quantities that are proportional to the same quantity are proportional to each other, it follows that ln(EKG" max) T-wave is proportional to 1/(E–M)lusi. Hence, the quantity ln(EKG" max) T-wave for the ith consecutive heartbeat can serve as an alternative or simultaneous index of lusitropic function. Since it is easily calculated from the existing data stream, the algorithm can plot $\ln(EKG" \ max)_{T-wave}$ as a function of 1/(E–M)lusi, and calculate the slope and intercept of the resulting function in a cumulative, epochal, or running fashion. This will increase the robustness of the system, since if one data stream drops out, its quantity can then be easily interpolated from the other and serves as a reality check on the other measurements. The changes in slope of the function that relates these two noninvasive indices may indicate subtle changes in inotropic function.
8) Simultaneously, the algorithm calculates (E–M)ino. This metric of the contractile, inotropic function of the myocardium shortens with increasing inotropy, as measured by the natural log of the first derivative of the left ventricular pressure in systolic contraction, that is, ln(LVP' max).

9) The E-event in (E–M)ino is the time of the second derivative maximum in the EKG voltage(t) function that corresponds nearly to the Q-wave in the QRS complex that heralds electrical systole on the EKG.
10) The inotropic M-event is the time of the maximum value of the second derivative of the phonocardiogram amplitude(t) function that corresponds to the S1 heart sound can be seen on a Wiggers Diagram, yielding:

$$\ln(LVP' \text{ max}) = A3 + B3/(E-M)ino \quad \text{Equation 3}$$

11) An alternative inotropic M-event can be derived from the cardiac seismogram. This can be the peak labeled "MC" denoting mitral valve closure.
12) The M-event can optionally be the peak in the first or second derivative of the cardiac seismogram that occurs just prior to MC. The optimal embodiment still needs to be determined empirically.
13) There exists an intropic interval (E–Et) that derives entirely from the EKG voltage as a function of time data steam having properties similar to (E–M)ino. Here, the E event is still the time of the second derivative EKG voltage(t) maximum that corresponds to the Q-wave of the QRS complex that heralds electrical systole. The Et event is the time of the second derivative EKG voltage(t) peak that corresponds to the beginning of the T-wave. In the second derivative, the T-wave has 2 peaks, separated by a time interval Delta $t''_{T\text{-}wave}$. The Et event corresponds to the first of these two peaks in the second derivative of the T-wave. There is evidence to show that, in cardiac systole, $$\ln(LVP' \text{ max}) = A4 + B4/(E-Et) \quad \text{Equation 4}$$

Again, since $1/(E-Et)$ and $1/(E-M)ino$ are both proportional to $\ln(LVP' \text{ max})$, that they are proportional to each other. It follows that (E–Et) and (E–M)lusi are also linearly proportional. The algorithm can map (E–Et) to (E–M)lusi in a way that increases the robustness of the system and allows missing data points to be interpolated from the linear relation. The fitting parameters of the linear relation can be calculated cumulatively, by data epoch, or in running fashion. We hypothesize that changes in the slope of this relation may indicate subtle changes in inotropic function which can be tested empirically. The time intervals (E–Et) and Delta $t''_{T\text{-}wave}$ may yield information about circulating cation concentration in the blood. For instance, Delta $t''_{T\text{-}wave}$ may correlate usefully with K+ concentration. Alternatively, the integral under the T-wave between the limits of the two EKG″ peaks in the T-wave that define Delta $t''_{T\text{-}wave}$ may serve the same purpose. $1/(E-Et)$ may predict circulating Ca++ in a way that is actionable, once the functions are appropriately calibrated with real Ca++ values.

14) Having the two metrics for both ln(LVP' max) and ln(LVP' min) for the ith consecutive heartbeat, and following the example in the Abstract, we want to create a metric of the ratio of [LVP' min/LVP' max] knowing that the ratio is greater than 1 in health, but that it decreases rapidly in septic shock, and deteriorates further in the natural history of the condition.
15) But by the properties of logarithms, $$\ln(\text{abs}(LVP' \text{ min})/LVP' \text{ max}) = \ln(LVP' \text{ min}) - \ln(LVP' \text{ max}) \quad \text{Equation 5}$$

We can substitute for the terms in the right hand side of eq. 5 such that $$\ln(\text{abs}(LVP' \text{ min})/LVP' \text{ max}) = [A1 + B1/(E-M)lusi] - [A3 + B3/(E-M)ino]$$

Rearranging terms, $$\ln(\text{abs}(LVP' \text{ min})/LVP' \text{ max}) = [A1-A3] + B1/(E-M)lusi - B3/(E-M)ino \quad \text{Equation 6}$$

Empirically, it is useful to create a large library of data taken from hundreds or thousands of cardiac catheterizations of the Left Ventricle with simultaneous values of (E–M)lusi, (E–M)ino, LVP' max, and LVP' min. This can be combined with data on height, weight, gender, age, rhythm, QRS width, Q–T interval, $\ln(EKG'' \text{ max})_{T\text{-}wave}$, and $1/(E-Et)$ for each heartbeat in the data set. From this data, we create a look-up table for expected values of A1, B1, A3, and B3, which is not necessary presently for creating a non-invasive metric that tracks linearly with the lusitropic/inotropic ratio as described in the Abstract. We know empirically from the Abstract that for pigs in robust health the ratio LVP' min/LVP' max has a value around 1.4. The natural log of 1.4 is about ⅓. Assume that A1 and A3 are about the same size. So, they cancel out in Eq. 6. Then, $$B1/(E-M)lusi - B3/(E-M)ino = \tfrac{1}{3} \text{From Equation 6}$$

B1 and B2 are constants. Assuming a state of health, or physiologic non-decompensation, for a particular patient, and that the patient had been previously studied sufficiently in that state so that we are given mode and mean values of (E–M)lusi and (E–M)ino in that same state of health. Since $1-\tfrac{2}{3}=\tfrac{1}{3}$, we arbitrarily adjust B1 and B2 so that $$B1/(E-M)lusi = 1, \text{ and}$$

$$B2/(E-M)ino = \tfrac{2}{3}$$

and at least heuristically, B1 and B2 are determined.
For the purpose of monitoring, we create a function $$Qi = \exp(B1/(E-M)lusi - B3/(E-M)ino) \quad \text{Equation 7}$$

where i is the ith heartbeat.

This useful function serves as a noninvasive metric of the lusitropic/inotropic ratio described in the Abstract. The monitoring process described herein can be used over hours, days, months, or years. Further, we can examine the function Qbar=(1/i)Sigma(Qi) over a respiratory cycle, or an epoch of 'n' consecutive respiratory cycles, or in a running fashion. If the function Qbar were to suddenly deteriorate, that might be an early signal that the patient was struggling with septic shock. If the patient's personal value of Qbar were well known from long and prior measurement, or calculated on admission to an ICU before the placement of a central line, and it were to suddenly decrease relative to baseline, the clinician is given cause to think that some septic process had been initiated, just like in the pig experiment in the Abstract. In a patient with a long history of ischemic cardiomyopathy, or HFpEF, then $1/(E-M)lusi$ would be a smaller quantity than normal, and hence the quantity $1/(E-M)lusi-1/(E-M)ino$ would have a smaller baseline level. Still, if that patient were to be admitted to the ICU where a central line was started, and the quantity $1/(E-M)lusi-1/(E-M)ino$ were to suddenly deteriorate as shown in the Abstract, a clinician could make the same inference about sepsis as in the case of a healthy individual. If this co-morbid patient were admitted to the OR for a hip fracture, it would be possible to download his values of (E–M)lusi and (E–M)ino from the cloud, and use them as the basis for monitoring for episodes of increased myocardial ischemia, and intervene appropriately with, for example, nitrates, oxygen, PEEP, or beta-blockers. For a patient is admitted to a hospital with heart failure, either with or without preserved ejection fraction, personal monitoring under the present system could be done while ambulatory constantly using smartphone connectivity. This capability would provide early warning signs of decompensation, to physicians, and to patients via text messages with appropriate instructions for remediation, and opportunities for intervention, to keep people with congestive heart failure out of the hospital, albeit on constant non-invasive monitoring.

16) Teachings in the '194 Patent are relevant with respect to the current system in measuring stroke volume, with the result that the product of stroke volume and heart rate measures cardiac output, based on using an (E–M) ino value. The two species of (E–M)ino values described here will serve, as will (E–Et), the latter being derived exclusively from the EKG signal. The '194 Patent teaches that ln(SV/EI) is proportional to ln(LVP' max). Here SV is stroke volume, and EI is the ejection interval. This is essentially a statement of a power law relating these two quantities. The quantity SV/EI is just the average rate of blood outflow from the LV into the aorta during systolic ejection. Knowing SV/EI from a non-invasive measurement, and knowing EI, allows the calculation of their product, stroke volume. A novel approach to measuring EI is to use the cardiac seismogram obtained from a precordial accelerometer that is part of, in one embodiment, a skin tattoo circuit with blue tooth connectivity as referenced earlier. To measure EI, one need only subtract the time of the peak designated AO from the time of peak AC as shown in the trace of the cardiac seismogram. An algorithm can be taught to look for these peaks following the EKG R-wave and T-wave respectively. Optionally, the seismogram can be used to identify the opening of the aortic valve AO, and the phonocardiogram can be used to identify the closing of the aortic valve as S2. In both these cases, the signal to noise ratio is optimally high.

From the teachings of the '194 Patent, $$\ln(SV/EI) = A4 + B4/(E-M)ino \quad \text{Equation 8}$$

Solving for SV, we get $$SV/EI = \exp[A4 + B4/(E-M)ino] = \exp(A4) * \exp(B4/(E-M)ino), \text{ and}$$

$$SV = E1 * \{\exp(A4) * \exp(B4/(E-M)ino)\} \quad \text{Equation 9}$$

Compared to the teachings of the '194 Patent, this approach has the advantage of being independent of the length of the patient's arteries, or the path length from the aortic valve to the detector over the radial artery. Using large amounts of patient data obtained using a fiducial cardiac output or stroke volume measurement technology, and combining that with patient data such as height, weight, age, and gender, it is possible to create a look-up table for expected values of A4 and B4 that are well founded in clinical reality. The system of the present invention allows for lusitropic, inotropic and stroke volume and cardiac output to be cheaply and non-invasively monitored on recumbent as well as ambulatory people, using just a skin tattoo circuit with MEMS transducers and blue tooth connectivity, and a smartphone with an Ethernet connection or otherwise connected to the Internet by simply wearing a skin patch and carrying a smartphone, a truly disruptive breakthrough in terms of the detection and mitigation of devastating and costly illness early in its natural history.

While it is the intention of this application to describe preferred embodiments of the instant invention, the present application should not to be read so as to preclude its coverage of similar embodiments of the system of the present invention that can be used to achieve the desired results of monitoring and patient care using the methods and the algorithms described herein.

What is claimed is:

1. A method for non-invasive monitoring of a patient to determine lusitropic myocardial function in relation to inotropic myocardial function comprised of the steps of:
    placing on the chest of a patient a non-invasive electronic heart function measurement device that provides an electronic signal related to said patient's electrical cardiac activity including QRS complexes;
    connecting the signal of said electronic heart measurement device to one input of a processing system;
    digitizing within said processing system said first input signal;
    placing on the chest of said patient a non-invasive mechanical heart function measurement device that provides an output related to mechanical cardiac activity;
    converting said output of said mechanical heart function measurement device into an electronic signal;
    connecting said converted electronic signal to a second input of said processing system;
    digitizing within said processing system said second input signal;
    applying to said digitized first signal a first algorithm to create a first value therefrom related to lusitropic myocardial function of said patient;
    applying to said digitized second signal a second algorithm to create a second value therefrom related to inotropic myocardial function of said patient;
    comparing said first value with said second value on a beat by beat basis to determine the ratio of lusitropic myocardial function to inotropic myocardial function for said patient in real time;
    providing an output of said processing system related to said ratio; and
    providing a humanly readable display related to said output of said processing system whereby real time review of lusitropic myocardial function, inotropic myocardial function, and the ratio of lusitropic myocardial function to inotropic myocardial function on a beat by beat basis is made available in order to assess myocardial well-being or myocardial pathology of said patient.

2. The method of claim 1 further comprising the additional steps of:
    providing an output of said processing system related to said first value; and
    providing a humanly readable display related to said output of said processing system whereby real time review of the lusitropic myocardial function on a beat by beat basis is made available in order to assess myocardial well-being or myocardial pathology of said patient.

3. The method of claim 1 further comprising the additional steps of:
    providing an output of said processing system related to said second value; and
    providing a humanly readable display related to said output of said processing system whereby real time review of the inotropic myocardial function on a beat by beat basis is made available in order to assess myocardial well-being or myocardial pathology of said patient.

4. The method of claim 1 in which said first algorithm is comprised of the steps of:
smoothing said digitized first signal;
differentiating said smoothed first signal in order to obtain a first time derivative of said first signal;
differentiating said first time derivative of said first signal to obtain a second time derivative of said first signal;
extracting from said second time derivative of said first signal the maximum value Q" which is in time related to the first peak of a Q wave wherein said Q wave is the first element in the QRS complex of an electrocardiogram as indicated on a standard Wiggers Diagram;
extracting from said second time derivative of said first signal the maximum value T" which is in time related to the first peak of a T wave which follows an S wave of said QRS complex marking the end of an absolute refractory period of said first signal; and
calculating a value by mapping 1/(T"−Q") to the natural logarithm of LVP' max, the peak value of the first time derivative of left ventricle pressure;
whereby said value is related to inotropic function.

5. The method of claim 1 in which said first algorithm is comprised of the steps of:
smoothing said digitized first signal;
differentiating said smoothed first signal in order to obtain a first time derivative of said first signal;
differentiating said first time derivative of said first signal to obtain a second time derivative of said first signal;
extracting from said second time derivative of said first signal the maximum value Q" which is in time related to the first peak of a Q wave wherein said Q wave is the first element in the QRS complex of an electrocardiogram as defined in a standard Wiggers Diagram; and
calculating a value by mapping 1/(S1"−Q"), the inverse of the difference in time between S1" which is in time related to a first heart sound as indicated on said Wiggers Diagram and said Q" to the natural logarithm of LVP' max, the peak value of left ventricle pressure, whereby said value is related to inotropic function.

6. The method of claim 1 in which said second algorithm is comprised of the steps of:
smoothing said digitized second signal;
differentiating said smoothed second signal in order to obtain a first time derivative of said second signal;
differentiating said first time derivative of said second signal to obtain a second time derivative of said second signal;
transforming by Fourier transform said second time derivative of said second signal;
passing said transformed second time derivative of said second signal through a low pass filter to obtain a transformed second time derivative of said second signal that is limited to frequencies below 50 hertz;
extracting from said frequency bounded second time derivative of said second signal the maximum value S2" which is in time related to a second heart sound as indicated on a standard Wiggers Diagram; and
calculating a value by mapping 1/(S2"−T"), the inverse of the difference in time between S2" and the maximum value T" wherein T" is determined by said first algorithm and is in time related to the first peak of a T wave which follows an S wave of the QRS complex as indicated on said standard Wiggers Diagram marking the end of an absolute refractory period of said first signal, to the natural logarithm of the absolute value of the minimum value of the first derivative of left ventricle pressure;
whereby said value is related to lusitropic function.

7. The method of claim 1 in which said second algorithm is comprised of the steps of:
smoothing said digitized second signal;
differentiating said smoothed second signal to obtain a first time derivative of said second signal;
differentiating said first time derivative of said second signal to obtain a second time derivative of said second signal;
transforming by Fourier transform said second time derivative of said second signal;
passing said transformed second time derivative of said second signal through a low pass filter to obtain a transformed second derivative of said second signal that is limited to frequencies below 50 hertz;
extracting from said frequency bounded second time derivative of said second signal the maximum value S1" which is in time related to a first heart sound as indicated on a standard Wiggers Diagram; and
calculating a value by mapping 1/(S1"−Q"), the inverse of the difference in time between S1" and the maximum value Q" wherein Q" is determined by said first algorithm and is in time related to the first peak of a Q wave wherein said Q wave is the first element in the QRS complex as indicated in said Wiggers Diagram, to 1/(T"−Q"), the inverse of the difference in time wherein T" is determined by said first algorithm and is in time related to the first peak of a T wave which follows an S wave of said QRS complex marking the end of an absolute refractory period of said first signal;
whereby said value is related to inotropic function.

8. The method of claim 1 in which said second algorithm is comprised of the steps of:
transforming by Fourier transform said digitized second signal;
passing said transformed second signal through a low pass filter to obtain a transformed second signal limited to frequencies below 50 hertz;
smoothing said frequency bounded second signal;
differentiating said smoothed frequency bounded second signal in order to obtain a first time derivative of said smoothed frequency bounded second signal;
differentiating said first time derivative of said smoothed frequency bounded second signal in order to obtain a second time derivative of said smoothed frequency bounded second signal;
extracting from said second derivative of said smoothed frequency bounded second signal S2" which is in time related to a second heart sound as indicated on a standard Wiggers Diagram; and
calculating a value by mapping 1/(S2"−T"), the inverse of the difference in time between S2" and the maximum value of T" wherein T" is determined by said first algorithm and is in time related to the first peak of a T wave which follows an S wave of the QRS complex of said standard Wiggers Diagram marking the end of the absolute refractory period of said first signal, to the natural logarithm of the absolute value of the minimum value of the first derivative of left ventricle pressure;
whereby said value is related to lusitropic function.

9. The method of claim 1 in which said second algorithm is comprised of the steps of:
transforming by Fourier transform said digitized second signal;

passing said transformed second signal through a low pass filter to obtain a transformed second signal that is limited to frequencies below 50 hertz;

smoothing said frequency bounded second signal;

differentiating said smoothed frequency bounded second signal in order to obtain a first time derivative of said smoothed frequency bounded second signal;

differentiating said first time derivative of said smoothed frequency bounded second signal in order to obtain a second time derivative of said smoothed frequency bounded second signal;

extracting from said second time derivative of said smoothed frequency bounded second signal the maximum value S1" which is in time related to a first heart sound as indicated on a standard Wiggers Diagram; and calculating a value by mapping 1/(S1"−Q"), the inverse of the difference in time between S1" and the maximum value Q" wherein Q" is determined by said first algorithm and is in time related to the first peak of a Q wave wherein said Q wave is the first element in the QRS complex as indicated in said Wiggers Diagram, to 1/(T"−Q"), the inverse of the difference in time wherein T" is determined by said first algorithm and is in time related to the first peak of a T wave which follows an S wave of said QRS complex marking the end of the absolute refractory period of said first signal;

whereby said value is related to inotropic function.

10. A system for non-invasive monitoring of cardiac activity comprising:
a non-invasive electronic heart function measurement device providing a first electronic signal related to electrical cardiac activity including QRS complexes;
a non-invasive mechanical heart function measurement device providing an output related to mechanical cardiac activity;
a converting unit connected to said mechanical heart function measurement device for converting the output of said device into a second electronic signal related to said mechanical cardiac activity;
a processing unit under the control of a first algorithmic program and under the control of a second algorithmic program into which are input said first electronic signal and said second electronic signal, the processing unit configured to provide a real time review of lusitropic myocardial function, inotropic myocardial function, and the ratio of lusitropic myocardial function to inotropic myocardial function on a beat by beat basis in order to assess myocardial well-being or myocardial pathology;
a connection from the output of said electronic heart function measurement device to the input of said processing unit;
a connection from the output of said converting unit to the input of said processing unit; and
a humanly readable display connected to the output of said processing unit, said display providing for the real time review of lusitropic myocardial function, inotropic myocardial function, and the ratio of lusitropic myocardial function to inotropic myocardial function on a beat by beat basis in order to assess myocardial well-being or myocardial pathology.

11. The system of claim 10 in which said first algorithmic program is comprised of the steps of:
digitizing said first electronic signal;
smoothing said digitized first signal;
differentiating said smoothed first signal in order to obtain a first time derivative of said first signal;
differentiating said first time derivative of said first signal to obtain a second time derivative of said first signal;
extracting from said second time derivative of said first signal the maximum value Q" which is in time related to the first peak of a Q wave wherein said Q wave is the first element in the QRS complex of an electrocardiogram as indicated on a standard Wiggers Diagram;
extracting from said second time derivative of said first signal the maximum value T" which is in time related to the first peak of a T wave which follows an S wave of said QRS complex marking the end of an absolute refractory period of said first signal; and
calculating a value by mapping 1/(T"−Q") to the natural logarithm of LVP' max, the peak value of the first time derivative of left ventricle pressure;
whereby said value is related to inotropic function.

12. The system of claim 10 in which said first algorithmic program is comprised of the steps of:
digitizing said first electronic signal;
smoothing said digitized first electronic signal;
differentiating said smoothed first signal in order to obtain a first time derivative of said first signal;
differentiating said first time derivative of said first signal to obtain a second time derivative of said first signal;
extracting from said second time derivative of said first signal the maximum value Q" which is in time related to the first peak of a Q wave wherein said Q wave is the first element in the QRS complex of an electrocardiogram as defined in a standard Wiggers Diagram; and
calculating a value by mapping 1/(S1"−Q"), the inverse of the difference in time between S1" which is in time related to a first heart sound as indicated on said Wiggers Diagram and said Q" to the natural logarithm of LVP' max, the peak value of left ventricle pressure;
whereby said value is related to inotropic function.

13. The system of claim 10 in which said second algorithmic program is comprised of the steps of:
digitizing said second electronic signal;
smoothing said digitized second electronic signal;
differentiating said smoothed second signal in order to obtain a first time derivative of said second signal;
differentiating said first time derivative of said second signal to obtain a second time derivative of said second signal;
transforming by Fourier transform said second time derivative of said second signal;
passing said transformed second time derivative of said second signal through a low pass filter to obtain a transformed second time derivative of said second signal that is limited to frequencies below 50 hertz;
extracting from said frequency bounded second time derivative of said second signal the maximum value S2" which is in time related to a second heart sound as indicated on a standard Wiggers Diagram; and
calculating a value by mapping 1/(S2"−Q"), the inverse of the difference in time between S2" and the maximum value T" wherein T" is determined by said first algorithm and is in time related to the first peak of a T wave which follows an S wave of the ORS complex as indicated on said standard Wiggers Diagram marking the end of the absolute refractory period of said first signal, to the natural logarithm of the absolute value of the minimum value of the first derivative of left ventricle pressure;
whereby said value is related to lusitropic function.

14. The system of claim 10 in which said second algorithmic program is comprised of the steps of:
- digitizing said second electronic signal;
- smoothing said digitized second electronic signal;
- differentiating said smoothed second signal to obtain a first time derivative of said second signal;
- differentiating said first time derivative of said second signal to obtain a second time derivative of said second signal;
- transforming by Fourier transform said second time derivative of said second signal;
- passing said transformed second time derivative of said second signal through a low pass filter to obtain a transformed second derivative of said second signal that is limited to frequencies below 50 hertz;
- extracting from said frequency bounded second time derivative of said second signal the maximum value S1" which is in time related to a first heart sound as indicated on a standard Wiggers Diagram; and
- calculating a value by mapping 1/(S1"−Q"), the inverse of the difference in time between S1" and the maximum value Q" wherein Q" is determined by said first algorithm and is in time related to the first peak of a Q wave wherein said Q wave is the first element in the QRS complex as indicated in said Wiggers Diagram, to 1/(T"−Q"), the inverse of the difference in time wherein T" is determined by said first algorithm and is in time related to the first peak of a T wave which follows an S wave of said QRS complex marking the end of the absolute refractory period of said first signal;
- whereby said value is related to inotropic function.

* * * * *

UNITED STATES PATENT AND TRADEMARK OFFICE
CERTIFICATE OF CORRECTION

| | |
|---|---|
| PATENT NO. | : 10,918,300 B2 |
| APPLICATION NO. | : 16/108846 |
| DATED | : February 16, 2021 |
| INVENTOR(S) | : Robert Alan Hirsh |

It is certified that error appears in the above-identified patent and that said Letters Patent is hereby corrected as shown below:

In the Claims

Column 16, Line 57, the variable reading:
-1/(S"-Q")-
Should read:
--1/(S"-T")--.

Signed and Sealed this
Third Day of September, 2024

Katherine Kelly Vidal
*Director of the United States Patent and Trademark Office*